(12) United States Patent
Boutoussov et al.

(10) Patent No.: US 10,321,957 B2
(45) Date of Patent: *Jun. 18, 2019

(54) SURGICAL LASER CUTTING DEVICE

(71) Applicant: BIOLASE, INC., Irvine, CA (US)

(72) Inventors: Dmitri Boutoussov, Dana Point, CA (US); Vladimir Netchitailo, Livermore, CA (US); Amado Carino, Laguna Beach, CA (US)

(73) Assignee: BIOLASE, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,530

(22) Filed: May 1, 2018

(65) Prior Publication Data
US 2018/0318008 A1 Nov. 8, 2018

Related U.S. Application Data

(63) Continuation of application No. 13/633,967, filed on Oct. 3, 2012, now Pat. No. 9,956,039.
(Continued)

(51) Int. Cl.
A61B 18/22 (2006.01)
A61B 18/26 (2006.01)
A61B 18/20 (2006.01)

(52) U.S. Cl.
CPC ............. *A61B 18/22* (2013.01); *A61B 18/26* (2013.01); *A61B 2018/208* (2013.01);
(Continued)

(58) Field of Classification Search
CPC ... A61B 18/22; A61B 18/26; A61B 2018/208; A61B 2018/2211; A61B 2018/2222;
(Continued)

(56) References Cited

U.S. PATENT DOCUMENTS 4,653,495 A   3/1987   Nanaumi
4,686,979 A   8/1987   Gruen et al.
(Continued)

FOREIGN PATENT DOCUMENTS

DE   102005057617   6/2007
EP   2763618        8/2014
(Continued)

OTHER PUBLICATIONS

United States Patent and Trademark Office; PCT International Search Report, Issued in Connection to PCT/US12/58536; dated Jan. 10, 2013; 3 pages; US.
(Continued)

*Primary Examiner* — Scott Luan
(74) *Attorney, Agent, or Firm* — Greenberg Traurig LLP

(57) ABSTRACT

Provided is a surgical handpiece for providing an electromagnetic cutting blade. The handpiece, comprises a body portion having an input end and an output end, a plurality of optical fibers for receiving laser energy having a wavelength within a predetermined wavelength range, wherein the optical fibers are received in the body portion at the input end and extend to the output end, and an optical fiber transition region within the body portion for arranging the plurality of optical fibers into a predetermine cutting shape at the output end, wherein laser energy transmitted from the arranged optical fibers at the output end interact with water molecules near the surgical target to generate micro-explosions that result in a cutting effect.

28 Claims, 9 Drawing Sheets

Related U.S. Application Data

(60) Provisional application No. 61/542,712, filed on Oct. 3, 2011.

(52) U.S. Cl.
CPC ............ *A61B 2018/20351* (2017.05); *A61B 2018/20359* (2017.05); *A61B 2018/225* (2013.01); *A61B 2018/2211* (2013.01); *A61B 2018/2222* (2013.01); *A61B 2018/2266* (2013.01); *A61B 2018/2288* (2013.01); *A61B 2018/263* (2013.01); *A61B 2218/002* (2013.01); *A61B 2218/005* (2013.01)

(58) Field of Classification Search
CPC ...... A61B 2018/225; A61B 2018/2266; A61B 2018/2288; A61B 2018/263; A61B 2018/002; A61B 2018/005; A61B 2018/20351; A61B 2018/20359
See application file for complete search history.

(56) References Cited

U.S. PATENT DOCUMENTS

| | | | |
|---|---|---|---|
| 5,071,422 | A | 12/1991 | Watson et al. |
| 5,250,045 | A | 10/1993 | Bohley |
| 5,395,361 | A | 3/1995 | Fox et al. |
| 6,106,516 | A | 8/2000 | Massengill |
| 6,162,052 | A | 12/2000 | Kokubu |
| 6,203,537 | B1 | 3/2001 | Adrian |
| 6,464,694 | B1 | 10/2002 | Massengill |
| 6,724,958 | B1 | 4/2004 | German et al. |
| 9,956,039 | B2 | 5/2018 | Boutoussov |
| 2005/0080404 | A1 | 4/2005 | Jones et al. |
| 2005/0281887 | A1 | 12/2005 | Rizoiu et al. |
| 2006/0189965 | A1 | 8/2006 | Litvak et al. |
| 2008/0058783 | A1 | 3/2008 | Altshuler et al. |
| 2008/0287941 | A1 | 11/2008 | Jones et al. |
| 2012/0015319 | A1 | 1/2012 | Jones et al. |
| 2013/0085486 | A1 | 4/2013 | Boutoussov |
| 2013/0310819 | A1* | 11/2013 | Neuberger ............ A61B 18/22 606/10 |

FOREIGN PATENT DOCUMENTS

| | | |
|---|---|---|
| JP | 60-148566 | 8/1985 |
| JP | 10-211211 | 8/1998 |
| JP | 11-511386 | 10/1999 |
| JP | 2003-135483 | 5/2003 |
| JP | 2014-528804 | 10/2014 |
| WO | 97/07928 | 3/1997 |
| WO | 99/22656 | 5/1999 |
| WO | 2013/052531 | 4/2013 |

OTHER PUBLICATIONS

United States Patent and Trademark Office; PCT Written Opinion of the International Searching Authority Issued in Connection to PCT/US12/58536; dated Jan. 10, 2013; 7 pages; US.

Canadian Intellectual Property Office; Issued in Connection to CA2850495; Apr. 21, 2015; 4 pages; Canada.

Japanese Patent Office, Notification of Reason for Rejection, Issued in Connection to JP2014-534649; dated Feb. 12, 2015; 6 pages; Japan.

European Patent Office; Extended European Search Report, Issued in Connection to EP12839133.1; dated May 22, 2015; 6 pages; Europe.

European Patent Office; Communication Pursuant to Article 94(3) EPC, Issued in Connection to EP12839133.1; dated Oct. 21, 2016; 3 pages; Europe.

European Patent Office; Communication Pursuant to Article 94(3) EPC, Issued in Connection to EP12839133.1; dated Jun. 27, 2017; 4 pages; Europe.

European Patent Office; Communication Pursuant to Article 94(3) EPC, Issued in Connection to EP12839133.1; dated Apr. 25, 2018; 3 pages; Europe.

\* cited by examiner

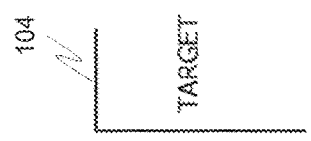
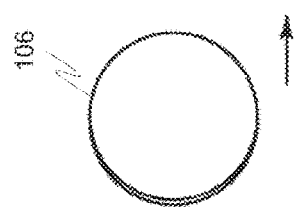
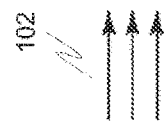
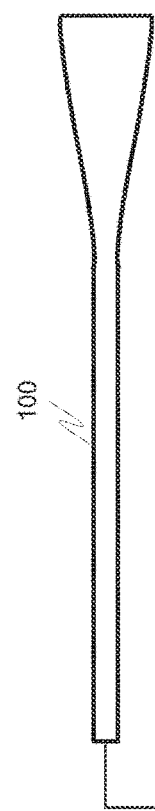
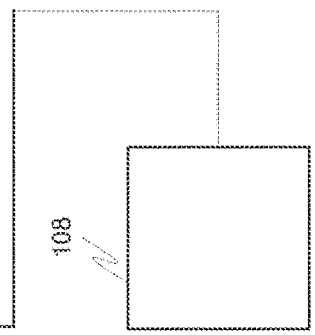
FIG. 2

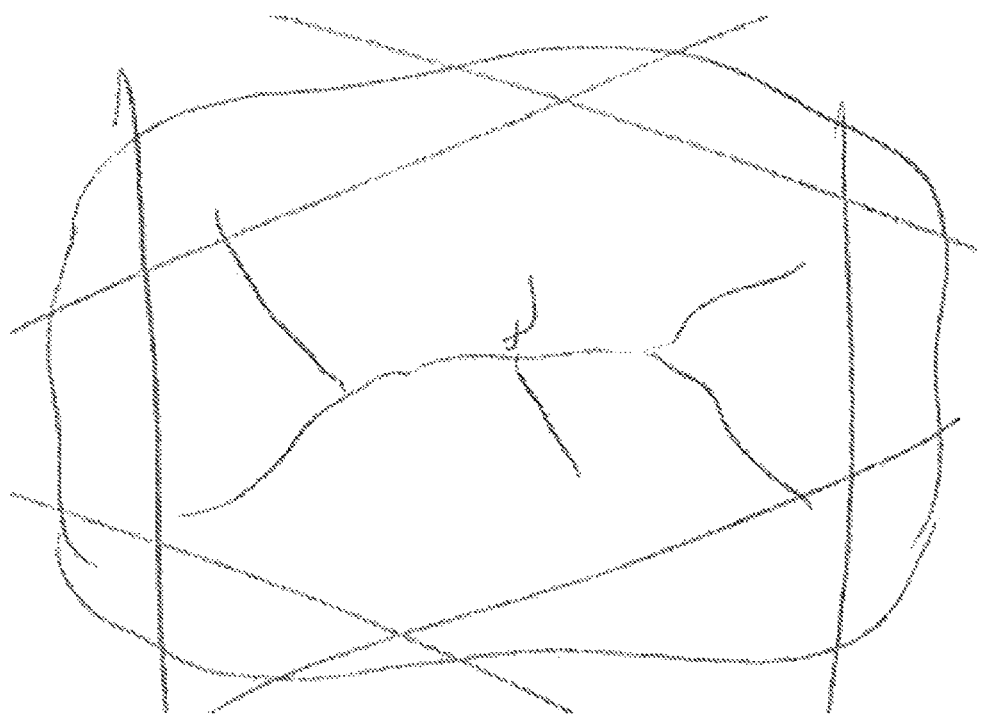
FIG. 9A
Sectioning tooth for crown preparation
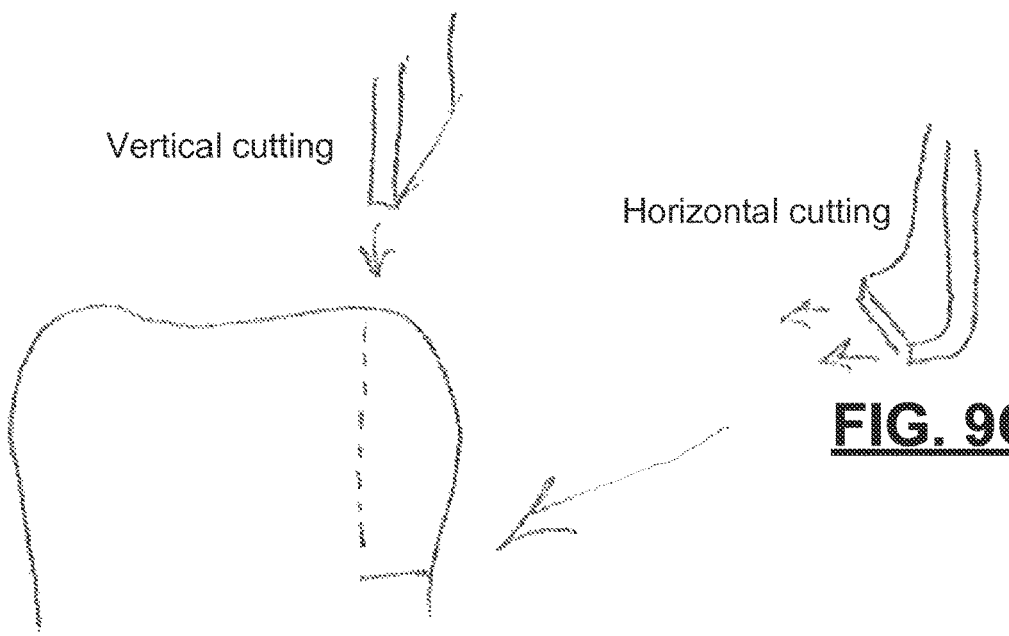
Vertical cutting
Horizontal cutting
FIG. 9C
FIG. 9B

SURGICAL LASER CUTTING DEVICE

CROSS-REFERENCE TO RELATED APPLICATIONS

This application is a continuation application and claims the benefit, and priority benefit, of U.S. patent application Ser. No. 13/633,967, filed Oct. 3, 2012, which claims the benefit and priority benefit of U.S. Provisional Application No. 61/542,712, filed Oct. 3, 2011, the entire contents of which are hereby incorporated by reference.

TECHNICAL FIELD

The technology described herein relates generally to medical lasers and, more particularly, to surgical applications of medical lasers.

BACKGROUND

Surgical instruments typically employed in applications such as orthopedics and oral surgery, in the ablation or cutting of hard tissue or bone, include high speed oscillating saws, manual saws or chisels. For example, depicted in FIG. 1 is an oscillating saw that may be operated by hand or that may be caused to vibrate by a motor in order to cut through a relatively large bone. A handle 10 has a cutting blade 20 disposed at the end of the handle. A sawing motion perpendicular to a direction of travel 30 can be used to saw through bone tissue 40. Devices such as these produce a cutting effect using friction. Friction, however, produces heat and the heat can cause the death of cells near the cut zone due to thermal necrosis.

SUMMARY

In accordance with the teachings provided herein, a surgical handpiece for providing an electromagnetic cutting blade is disclosed. The handpiece, comprises a body portion having an input end and an output end, a plurality of optical fibers for receiving laser energy having a wavelength within a predetermined wavelength range, wherein the optical fibers are received in the body portion at the input end and extend to the output end, and an optical fiber transition region within the body portion for arranging the plurality of optical fibers into a predetermine cutting shape at the output end, wherein laser energy transmitted from the arranged optical fibers at the output end react with fluid molecules near the surgical target to generate micro-explosions that result in a cutting effect.

BRIEF DESCRIPTION OF THE DRAWINGS

Depicted in FIG. 1 is an oscillating saw that may be operated by hand or that may be caused to vibrate by a motor in order to cut through a relatively large bone;

Depicted in FIG. 2 is an example laser handpiece device 100 that can be used for cutting bone or other hard biological material;

Figure 1:
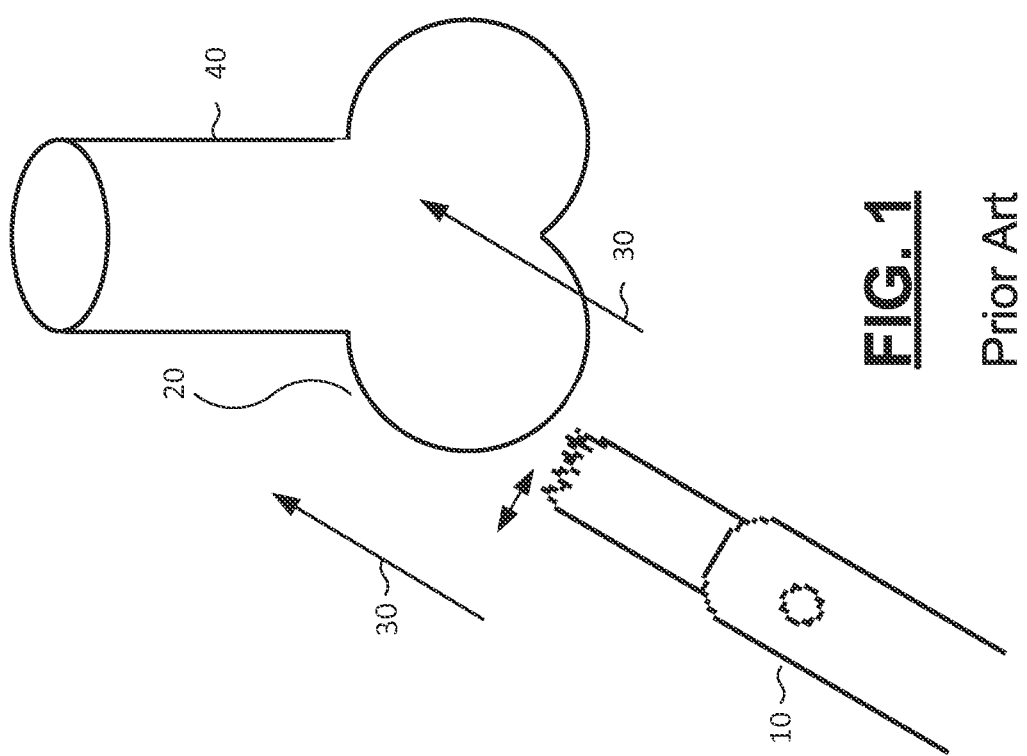
Figure 3A:
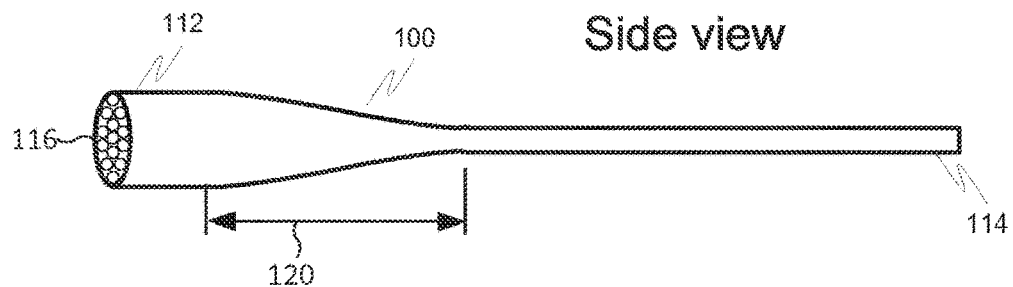
Figure 3B:
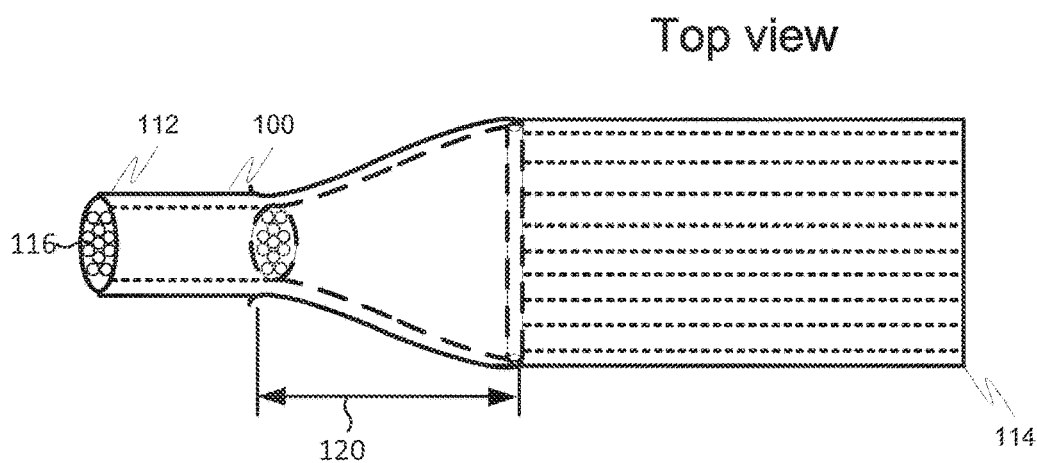
Figure 3C:
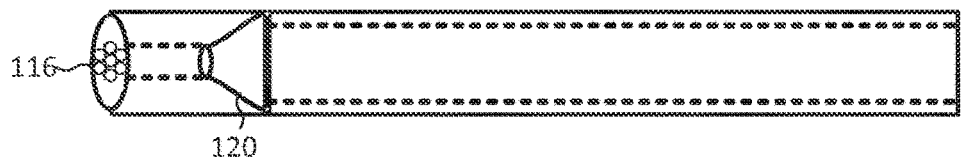
Figure 4A:
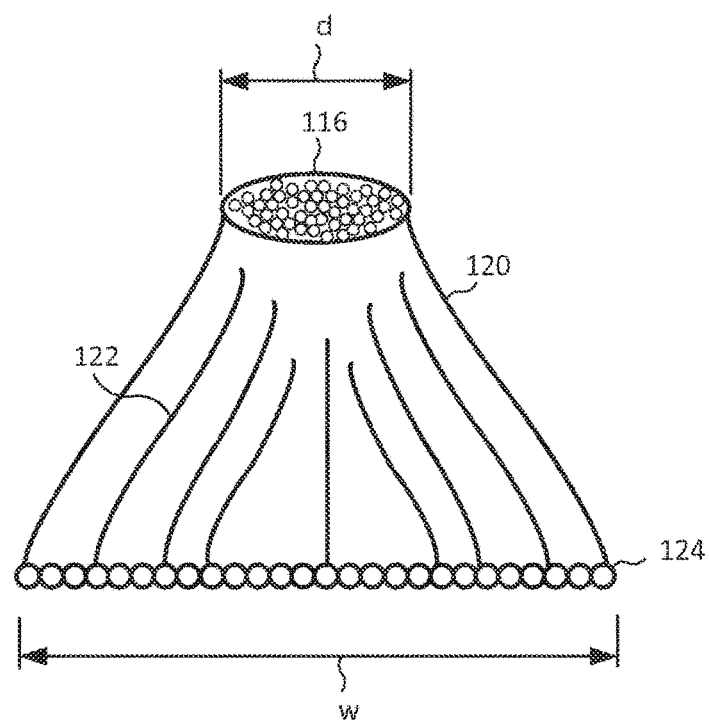
Figure 4B:
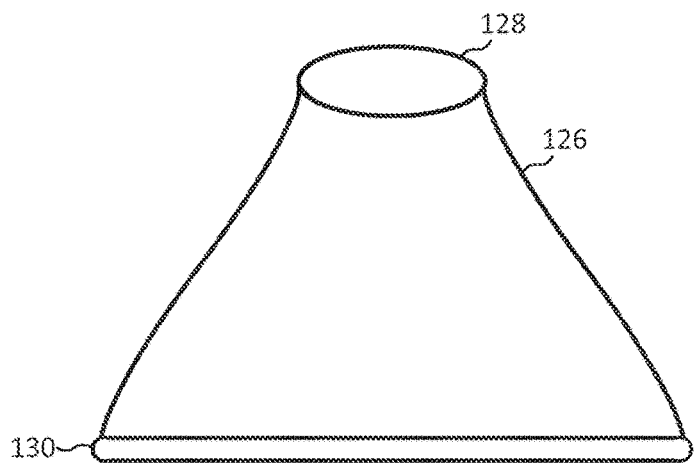
Figure 5A:
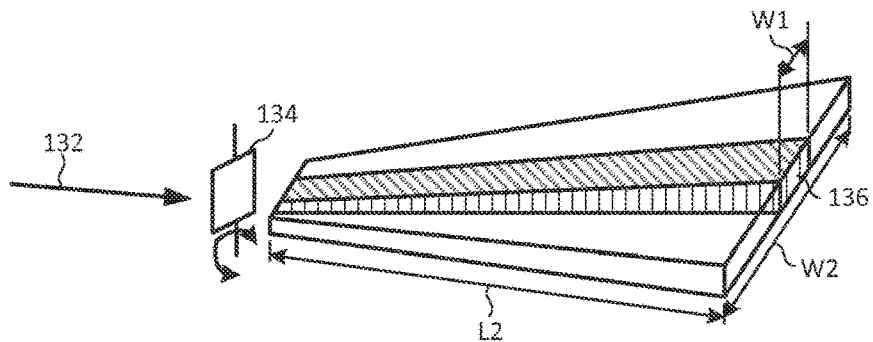
Figure 5B:
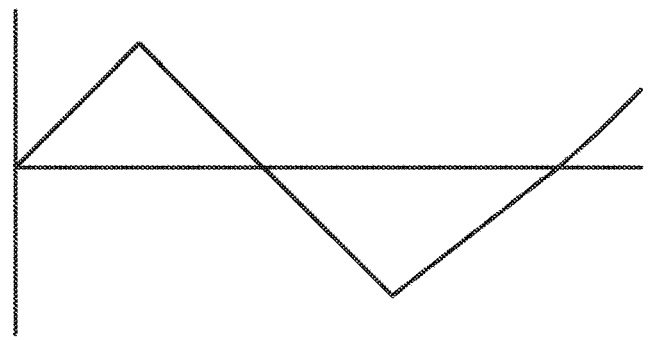
Figure 5C:
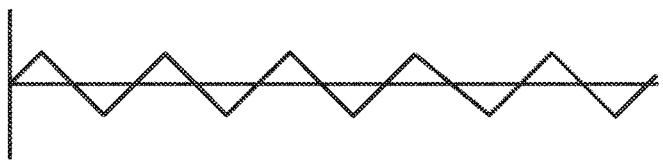
Figure 5D:
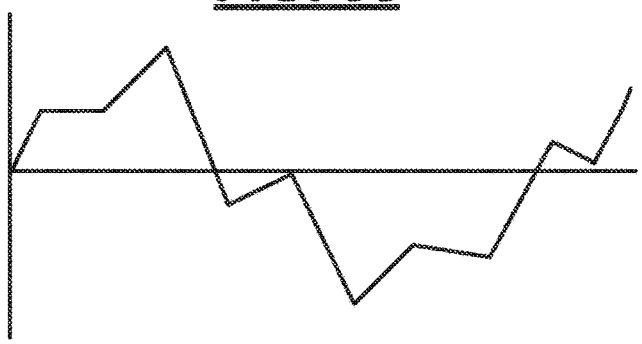
Figure 6A:
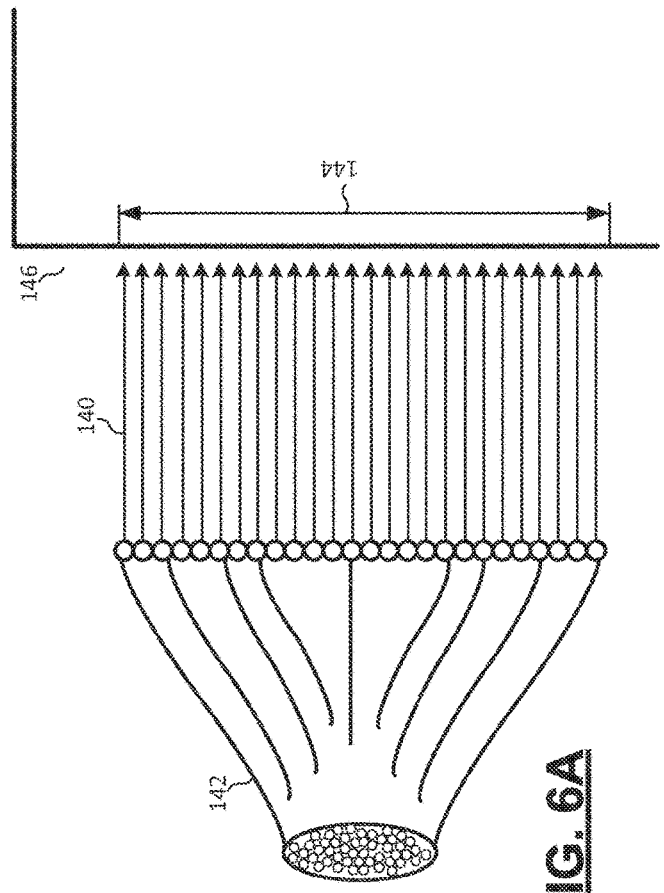
Figure 6B:
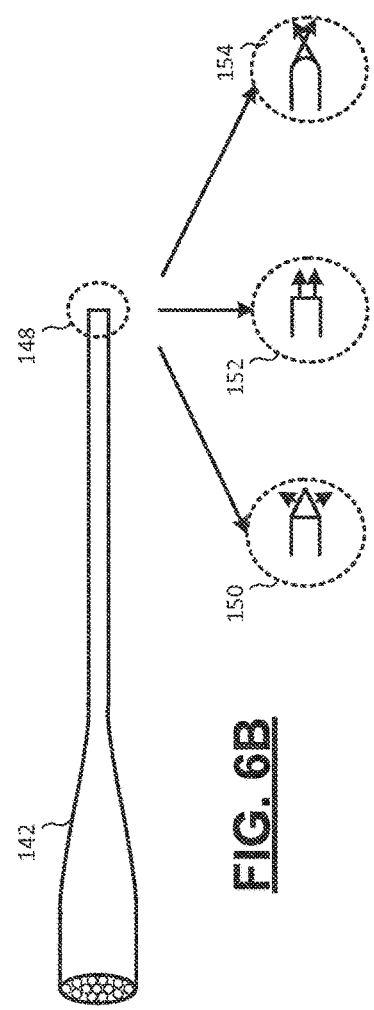
Figure 7A:
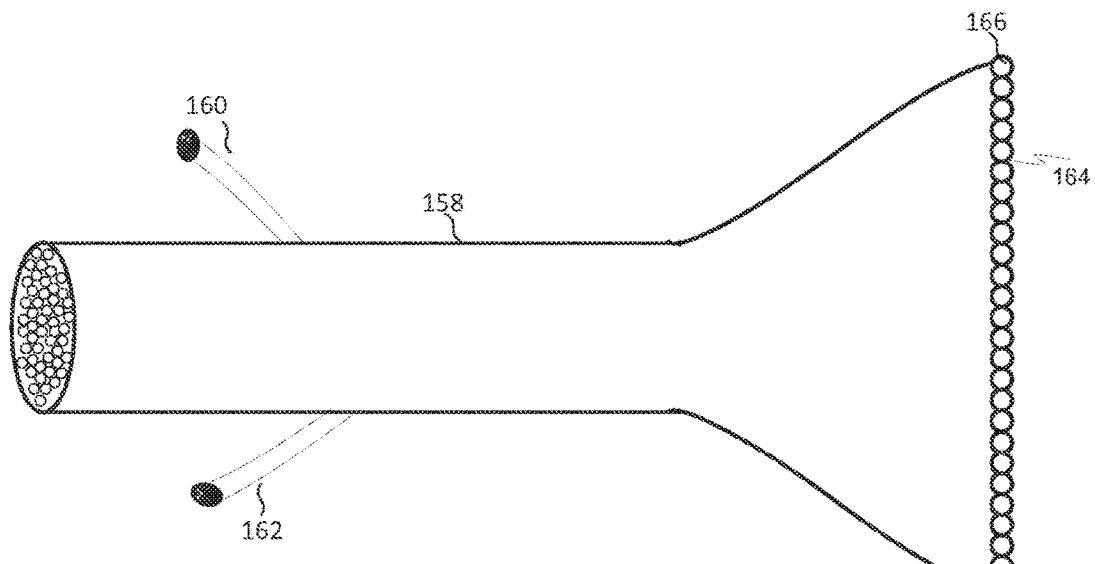
Figure 7B:
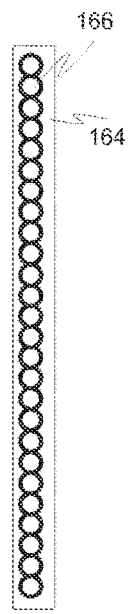

Depicted in FIG. 3A is a side view of an example laser handpiece device 100;

Depicted in FIG. 3B is a top view of the example laser handpiece device 100;

Depicted in FIG. 3C is a view of an example handpiece having a cylindrical shape;

Depicted in FIG. 4A is a view of the transition region 120;

Depicted in FIG. 4B is an example housing 126 for fanning out the optical fibers;

Depicted in FIG. 5A is an example system for dispersing collimated light 132 from a collimated laser source to the individual optical fibers that enter the handheld device;

Depicted in FIGS. 5B-5D are example control signals for controlling the scan rate of mirror 134;

FIG. 6A illustrates that electromagnetic energy 140 dispensed from an example handpiece 142 may be collimated and therefore will spread slowly as it propagates toward a cut zone 144 at a surgical target 146;

Depicted in FIG. 6B are various tips that may be applied to the end 148 of handpiece 142 to cause more spreading of the electromagnetic energy as it is dispensed to create a wider or thicker cut zone;

Depicted in FIG. 7A is an example handpiece 158 having a fluid inlet 160 and a gas inlet 162;

FIG. 7B illustrates example locations for water outlets 164 in a handpiece;

Depicted in FIGS. 8A-8F are example arrangements of the optical fibers at the output end of a handpiece; and FIGS. 9A-9C illustrates an example of sectioning the crown of the tooth for crown preparation.

DETAILED DESCRIPTION

Depicted in FIG. 2 is an example laser handpiece device 100 that can be used for cutting bone, tooth or other hard biological material. The handpiece 100 is an electromagnetic delivery device that functions as an electromagnetically induced disruptive cutter. The handpiece 100 directs electromagnetic energy 102 in the form of beams of laser energy into an interaction zone in close proximity to a surgical target 104 such as a bone, tooth, or other hard biological material. Fluid particles 106 such as water particles are also directed to the interaction zone.

The laser energy 102 interacts with fluid particles 106 in the interaction zone and with water molecules contained within the biological target. The laser energy is absorbed by and excites the fluid particles 106 and the water molecules resulting in sequential micro-explosions of the fluid particle and water molecules. These micro-explosions generate mechanical disruptive forces. The disruptive forces when applied to the biological target result in a cutting effect on the surface of the target.

The laser energy 102 is at a wavelength and energy level sufficient to excite micro-explosions in water molecules but not at levels sufficient to damage biological tissue. In the example system, typical values for total laser energy (energy emitted by all fibers) per laser pulse may range from about 0.05 J to about 2.0 J, and the energy may be generated with a wavelength ranging from about 2.75 µm to about 3.00 µm.

The fluid particles injected into the interaction zone perform a number of purposes. Some of the fluid particles absorb beams of light, explode, and impart a mechanical disruptive force to the target. Remaining portions of the fluid particles reduce the temperature surrounding the explosion so that living cells adjacent the target area will not be exposed to the extreme heat resulting in cell necrosis and death.

Very efficient tissue cutting without adjacent cells necrosis can be achieved using this technology. In the example system, individual beams are arranged parallel to each other in the same plane creating a linear segment of beams at a target that are sequential fired. This reduces the likelihood of a manual sweeping action being used to cut through tissue resulting in an efficient and accurately sized cut.

The handpiece 100 is coupled to an electromagnetic energy source 108 (i.e., laser energy source) which generates laser energy. The electromagnetic energy source 108 may include devices comprising mirrors, lenses, and other optical components for collimating and focusing generated laser energy. The generated laser energy is delivered to the handpiece 100 via a plurality of optical fibers 110 which extend into the interior of the handpiece 100.

The electromagnetic energy source 108 may include a variety of different lasers or other sources of light. The electromagnetic energy source 108 may use an erbium, chromium, yttrium, scandium, gallium garnet (Er, Cr:YSGG) solid state laser, which generates light having a wavelength in a range of approximately 2.70 to 2.80 μm. Laser systems used in other examples include an erbium, yttrium, aluminum garnet (Er:YAG) solid state laser, which generates radiation having a wavelength of 2.94 μm; a chromium, thulium, erbium, yttrium, aluminum garnet (CTE:YAG) solid state laser, which generates radiation having a wavelength of 2.69 μm; an erbium, yttrium orthoaluminate (Er:YAL03) solid state laser, which generates radiation having a wavelength in a range of approximately 2.71 to 2.86 μm; a holmium, yttrium, aluminum garnet (Ho:YAG) solid state laser, which generates radiation having a wavelength of 2.10 μm; a quadrupled neodymium, yttrium, aluminum garnet (quadrupled Nd:YAG) solid state laser, which generates radiation having a wavelength of 266 nm; excimer lasers, which generates radiation having a wavelength of 193-308 nm; a carbon dioxide (C02) laser, which generates radiation having a wavelength in a range of approximately 9.0 to 10.6 μm; and semiconductor diode lasers, which generate radiation having a wavelength in a range of approximately 400 to 1550 nm.

Depicted in FIG. 3A is a side view of an example laser handpiece device 100. The handpiece 100 includes an input end 112 and an output end 114. The input end 112 receives several optical fibers 116 through which electromagnetic energy is delivered to the handpiece 100. Laser beams that are directed to the interaction zone at the surgical target exit the handpiece at the output end 114. In the device illustrated, the height of the handpiece is larger at the input end than at the output end. This configuration reflects that at the input end, in the example device, several optical fibers enter the handpiece in a honeycomb shaped bundle. In a transition region 120 in the handpiece, the optical fibers transition from a honeycomb shaped bundle to a flattened arrangement wherein at the output end the optical fibers are arranged in a flat parallel row of optical fibers.

Depicted in FIG. 3B is a top view of the example laser handpiece device 100. This view illustrates the flattening of the fiber optic bundle to a flat parallel row of optical fibers. In this example, the width of the handpiece is larger at the output end than at the input end also highlighting the transition of the optical fibers from a honeycomb shaped bundle to a flat arrangement.

Other physical configurations of the laser handpiece device can be constructed. Depicted in FIG. 3C is a view of an example handpiece having a cylindrical shape. At the input end several optical fibers 116 enter the handpiece in a honeycomb shaped bundle. In a transition region 120 in the handpiece, the optical fibers transition from a honeycomb shaped bundle to a flattened arrangement. At the output end the optical fibers are arranged in a flat parallel row of optical fibers. The diameter of this example device is sufficient to accommodate the honeycomb shaped bundle of optical fibers at the input end and the flat arrangement at the output end.

Depicted in FIG. 4A is a view of the transition region 120. A bundle of optical fibers 116 having a bundle diameter d enter the transition region. The optical fibers are separated from the bundle in the transition region and fan-out 122 of the optical fibers occurs. The optical fibers exit the transition region arranged in a flat parallel row of optical fibers 124 having a width w that is greater in magnitude than d.

Depicted in FIG. 4B is an example housing 126 for fanning out the optical fibers. The fibers may be fabricated of materials such as low OH quartz, germanium oxide, aluminum fluoride, or sapphire. The housing 126 could be constructed from glass, glass fiber, stainless steel or other suitable material. The housing 126 can receive a fiber optic bundle at an input opening 128 and dispense a flat parallel row of optical fibers at an output opening 130. The housing 126 has a transition region between the two openings 128, 130 to allow the optical fibers to separate from the bundle and fan-out.

The laser handpiece may be constructed with venous numbers of fibers, fiber dimensions and shapes. For example, the handpiece may comprise about 10 fibers for emitting 10 laser beams for cutting a 1 cm bone. As another example, about 50 fibers for emitting 50 beams may be employed for the cutting of a 5 cm bone.

The light in the fibers are collimated and concentrated to produce a very concentrated light in each optical fiber. Depicted in FIG. 5A is an example system for dispersing collimated light 132 from a collimated laser source to the individual optical fibers that enter the handheld device. One or more mirror(s) 134 or a prism direct collimated light from a collimated power source to specific regions 136 at which the inputs to the optical fibers are located. The mirrors disperse power to multiple fibers in a controlled manner so that the power in the individual fibers will be the same. The mirrors can be controlled in a periodic or non-linear manner, but controlled to ensure that the energy from the collimated light is dispersed evenly to the various optical fibers. This allows for an even distribution of the laser energy when it exits the handpiece. In this example system, the scanning beam has a width W1 at a distance L2=~2-5 cm and scanning width W2=~2-5 cm. By adjusting the scanning width W1 relative to W2, the power density of the light entering the optical fibers can be adjusted.

Depicted in FIGS. 5B-5D are example control signals for controlling the scan rate of mirror 134. FIG. 5B illustrates the use of a triangular shaped control signal. FIG. 5C illustrates the use of a higher frequency triangular shaped control signal. FIG. 5D illustrates the use of a non-linear control signal.

As illustrated in FIG. 6A, electromagnetic energy 140 dispensed from an example handpiece 142 may be collimated and therefore will spread slowly as it propagates toward a cut zone 144 at a surgical target 146. As illustrated in FIG. 6B, various lens tips may be applied to the end 148 of handpiece 142 to cause varied spreading of the electromagnetic energy as it is dispensed to different cut zones. Lens tips may also be used to cause clearer cuts. Tapered tip 150 may be used to direct the electromagnetic energy to the side as it leaves the handpiece. The use of rectangular tip 152 may not cause the electromagnetic energy to spread as it leaves the handpiece. Rounded tip 154 may be used to focus the electromagnetic energy at a specific distance from the handpiece. Use of tips with various shapes may be of particular interest in difficult to access areas, like periodontal pockets or root canal system in dentistry; or in the intervertibral disk area in the spine.

Depicted in FIG. 7A is an example handpiece 158 having a fluid inlet 160 and a gas inlet 162. The handpiece 158 also includes water outlets 164 between and/or around the fibers 166 as also illustrated in FIG. 7B. By inputting fluid such as water through fluid inlet 160 and pressurize gas such as forced air through the gas inlet 162, the handpiece 158 can expel fluid particles at a target via outlets 164 in addition to directing electromagnetic energy toward the target. The handpiece therefore can also function as a fluid router for injecting fluid particles into the interaction zone.

Figure 8A:
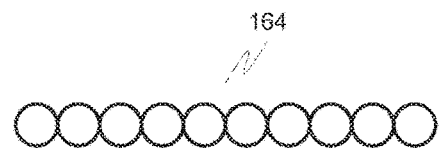
Figure 8B:
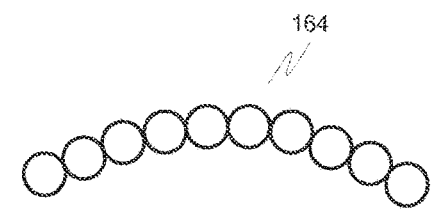
Figure 8C:
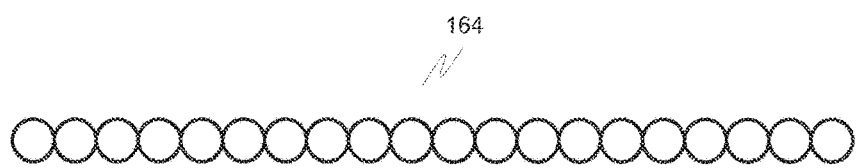
Figure 8D:
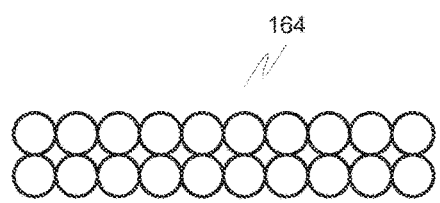
Figure 8E:
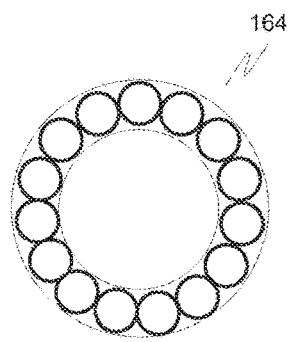
Figure 8F:
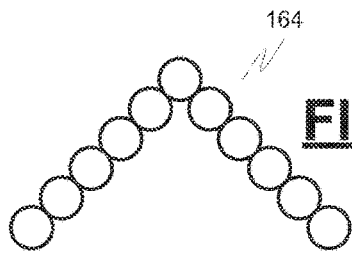

Depicted in FIGS. 8A-8D are example arrangements of the optical fibers at the output end of a handpiece. FIG. 8A illustrates an arrangement that could yield a standard cut length. FIG. 8B illustrates an arrangement that could result in a curved or non-linear cut. FIG. 8C illustrates an arrangement that can result in a longer cut length. FIG. 8D illustrates an arrangement that can result in a wider cut area. FIG. 8E illustrates an arrangement that can result in a circular cut. FIG. 8F illustrates an arrangement that can result in an angled cut. These examples illustrate that the optical fibers can be arranged in various shapes and lengths to create the optimal cutting pattern.

Depicted in FIGS. 9A-9C are examples of tooth crown sectioning with vertical (FIG. 9B) and horizontal (FIG. 9C) cutting tips.

This written description uses examples to disclose the invention, including the best mode, and also to enable a person skilled in the art to make and use the invention. The patentable scope of the invention may include other examples.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Further, as used in the description herein and throughout the claims that follow, the meaning of "each" does not require "each and every" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive of" may be used to indicate situations where only the disjunctive meaning may apply.

What is claimed is:

1. A surgical handpiece for providing an electromagnetic cutting blade, comprising:
    a body portion having an input end and an output end;
    a plurality of optical fibers configured and arranged for receiving laser energy having a wavelength within a predetermined wavelength range, wherein the optical fibers are received in the body portion at the input end and extend to the output end, the output end being substantially free of obstructions to the laser energy in the optical fibers; and
    an optical fiber transition region within the body portion for arranging the plurality of optical fibers into a predetermined cutting shape at the output end;
    a plurality of water outlets between and/or around the plurality of optical fibers, the plurality of water outlets configured to inject fluid particles into an interaction zone; and
    wherein the laser energy transmitted from the arranged optical fibers at the output end is configured to enter the interaction zone proximate a surgical target zone and interact with fluid particles in the interaction zone and with water molecules within the surgical target to generate a cutting effect to the surgical target,
    the optical fibers being, at a location within the body portion, grouped together in a bundle, and
    the optical fibers being, at the output end, strung out along a line that follows the predetermined cutting shape, wherein the spacing and arrangement of the optical fibers at the output end is different from the spacing and arrangement of the optical fibers at the input end, and
    the cutting effect producing, on the surgical target, a line of cutting that matches the predetermined cutting shape.

2. The handpiece according to claim 1, wherein the body portion further comprises a fluid inlet configured and arranged for receiving a fluid; and
    wherein the plurality of water outlets are configured and arranged for directing the received fluid at a surgical target.

3. The handpiece according to claim 2, wherein the body portion further comprises a gas inlet configured and arranged for receiving air; and
    wherein the plurality of water outlets are configured to direct the received air at the surgical target.

4. The handpiece according to claim 1, further comprising a transition housing configured and arranged for fanning out a bundle of the optical fibers.

5. The handpiece according to claim 4, wherein the transition housing is fabricated of at least one of solid glass, and stainless steel.

6. The handpiece according to claim 1, wherein transmitting ends of the plurality of optical fibers are arranged in a straight line.

7. The handpiece according to claim 1, wherein transmitting ends of the plurality of optical fibers are arranged in a curved line.

8. The handpiece according to claim 1, wherein transmitting ends of the plurality of optical fibers are arranged in two straight lines.

9. The handpiece according to claim 1, wherein the output end comprises a lens tip having at least one of a tapered shape, a rectangular shape, and a rounded shape.

10. The handpiece according to claim 1, wherein the predetermined wavelength range ranges from about 2.75 μm to about 3.00 μm.

11. The handpiece according to claim 1, wherein the fibers are fabricated from at least one of low OH quartz, germanium oxide, aluminum fluoride, and sapphire.

12. The handpiece according to claim 1, wherein the plurality of fibers comprise about 10 or about 50 fibers.

13. The handpiece according to claim 1, wherein the laser energy distributed at the output end ranges from about 0.05 J to about 2.0 J.

14. The handpiece according to claim 1, wherein transmitting ends of the plurality of fibers are arranged for a circular cut.

15. The handpiece according to claim 1, wherein transmitting ends of the plurality of fibers are arranged for an angled cut.

16. A surgical device comprising:
    a collimated laser source;
    a scanning element configured and arranged to receive laser energy from the laser source and generate a scanning beam for scanning the laser energy into a plurality of optical fibers; and
    a surgical handpiece configured for providing an electromagnetic cutting blade, the handpiece comprising:

a body portion configured to receive the plurality of optical fibers and having an optical fiber transition region within the body portion for arranging the plurality of optical fibers into a predetermined cutting shape at an output end of the body portion, the output end being substantially free of obstructions to the laser energy in the optical fibers;

a plurality of water outlets between and/or around the plurality of optical fibers, the plurality of water outlets configured to inject fluid particles into an interaction zone; and wherein the laser energy transmitted from the arranged optical fibers at the output end is configured to enter the interaction zone proximate a surgical target zone and interact with fluid particles in the interaction zone and with water molecules within the surgical target to generate a cutting effect to the surgical target, the optical fibers being, at a location within the body portion, grouped together in a bundle wherein the spacing and arrangement of the optical fibers at the output end is different from the spacing and arrangement of the optical fibers at an input end of the body portion; and the optical fibers being, at the output end, strung out along a line that follows the predetermined cutting shape; and the cutting effect producing, on the surgical target, a line of cutting that matches the predetermined cutting shape.

17. The device according to claim 16, wherein the scanning element comprises at least one of a mirror, and a prism.

18. The device according to claim 16, wherein the body portion further comprises a fluid inlet configured and arranged for receiving a fluid; and wherein the plurality of water outlets are configured and arranged for directing the received fluid at a surgical target.

19. The device according to claim 18, wherein the body portion further comprises a gas inlet configured and arranged for receiving air; and wherein the plurality of water outlets are configured to direct the received air at the surgical target.

20. The device according to claim 16, further comprising a transition housing configured and arranged for fanning out a bundle of the optical fibers.

21. The device according to claim 20, wherein the transition housing is fabricated of at least one of solid glass, and stainless steel.

22. The device according to claim 16, wherein transmitting ends of the plurality of optical fibers are arranged in a straight line.

23. The device according to claim 16, wherein transmitting ends of the plurality of optical fibers are arranged in a curved line.

24. The device according to claim 16, wherein transmitting ends of the plurality of optical fibers are arranged in two straight lines.

25. The device according to claim 16, wherein the output end comprises a lens tip having at least one of a tapered shape, a rectangular shape, and a rounded shape.

26. The device according to claim 16, wherein the laser energy distributed at the output end ranges from about 0.05 J to about 2.0 J.

27. The device according to claim 16, wherein transmitting ends of the plurality of fibers are arranged for a circular cut.

28. The device according to claim 16, wherein transmitting ends of the plurality of fibers are arranged for an angled cut.

* * * * *